`US005569215A`

United States Patent [19]

Crocker

[11] Patent Number: 5,569,215
[45] Date of Patent: Oct. 29, 1996

[54] LOW PROFILE INFUSION CATHETER

[75] Inventor: Michael Crocker, Mission Viejo, Calif.

[73] Assignee: Cardiovascular Dynamics, Inc., Irvine, Calif.

[21] Appl. No.: 467,856

[22] Filed: Jun. 6, 1995

Related U.S. Application Data

[63] Continuation of Ser. No. 83,021, Jun. 24, 1993, abandoned.

[51] Int. Cl.⁶ ..................................................... A61M 5/00
[52] U.S. Cl. ............................................ 604/264; 604/280
[58] Field of Search .................................. 604/49, 52–55, 604/39–45, 96, 258, 264, 173, 280–284; 606/194; 128/656–658

[56] References Cited

U.S. PATENT DOCUMENTS

| | | | |
|---|---|---|---|
| 3,155,097 | 11/1964 | Barron | 604/270 |
| 4,309,994 | 1/1982 | Grunwald | 604/284 |
| 4,406,656 | 9/1983 | Hattler et al. | 604/96 |
| 4,596,563 | 6/1986 | Pande | 604/280 |
| 4,638,805 | 6/1987 | Powell | 604/97 |
| 4,690,175 | 9/1987 | Ouchi et al. | 604/282 |
| 4,712,551 | 12/1987 | Rayhanabad | 604/96 |
| 4,739,768 | 4/1988 | Engelson . | |
| 4,762,128 | 8/1988 | Rosenbluth . | |
| 4,762,129 | 8/1988 | Bonzel . | |
| 4,775,371 | 10/1988 | Mueller, Jr. | 604/280 |
| 4,804,359 | 2/1989 | Grunwald et al. | 604/284 |
| 4,925,452 | 5/1990 | Melingshyn et al. | 604/284 |
| 4,927,418 | 5/1990 | Dake et al. . | |
| 4,968,306 | 11/1990 | Huss et al. . | |
| 4,968,307 | 11/1990 | Dake et al. . | |
| 4,981,478 | 1/1991 | Evard et al. . | |
| 4,995,865 | 2/1991 | Gahara et al. . | |
| 5,015,232 | 5/1991 | Maglinte | 604/96 |
| 5,021,044 | 6/1991 | Sharkawy . | |
| 5,026,357 | 6/1991 | Przuntek et al. . | |
| 5,041,101 | 8/1991 | Seder et al. | 604/284 |
| 5,061,273 | 10/1991 | Yock . | |
| 5,087,244 | 2/1992 | Wolinsky et al. . | |
| 5,108,368 | 4/1992 | Hammerslag et al. . | |
| 5,116,310 | 5/1992 | Seder et al. . | |
| 5,116,327 | 5/1992 | Seder et al. | 604/284 |
| 5,135,599 | 8/1992 | Martin et al. . | |
| 5,149,330 | 9/1992 | Brightbill . | |
| 5,176,661 | 1/1993 | Evard et al. . | |
| 5,213,576 | 5/1993 | Abiuso et al. . | |
| 5,232,444 | 8/1993 | Just et al. . | |
| 5,242,395 | 9/1993 | Maglinte | 604/96 |
| 5,254,089 | 10/1993 | Wang . | |
| 5,308,342 | 5/1994 | Sepetka et al. | 604/282 |
| 5,313,939 | 5/1994 | Gonzalez | 604/49 |
| 5,336,178 | 8/1994 | Kaplan et al. | 604/96 |

FOREIGN PATENT DOCUMENTS

| | | |
|---|---|---|
| 032225 | 6/1989 | European Pat. Off. . |
| 358117 | 3/1990 | European Pat. Off. . |
| 0567788 | 11/1993 | European Pat. Off. . |
| 4025503 | 5/1991 | Germany . |
| 8600232 | 1/1987 | WIPO . |
| 8909633 | 10/1989 | WIPO . |
| 9325265 | 12/1993 | WIPO . |

OTHER PUBLICATIONS

*Principles of Internal Medicine: Acute Myocardial Infraction*, by Richard C. Pasternak and Eugen Braunwald, 12th Ed. vol. 1 p. 953 1991.

Primary Examiner—John D. Yasko
Assistant Examiner—Mark Bockelman
Attorney, Agent, or Firm—Knobbe, Martens, Olson & Bear

[57] ABSTRACT

Disclosed is a low profile infusion catheter for medical use. The catheter comprises a proximal infusion lumen, which, in one embodiment, branches into two or more distal infusion lumen. Each of the distal fluid lumen is provided with at least one effluent flow port for infusion into the patient. Construction of the catheter provides a series of discrete flexibility zones.

10 Claims, 3 Drawing Sheets

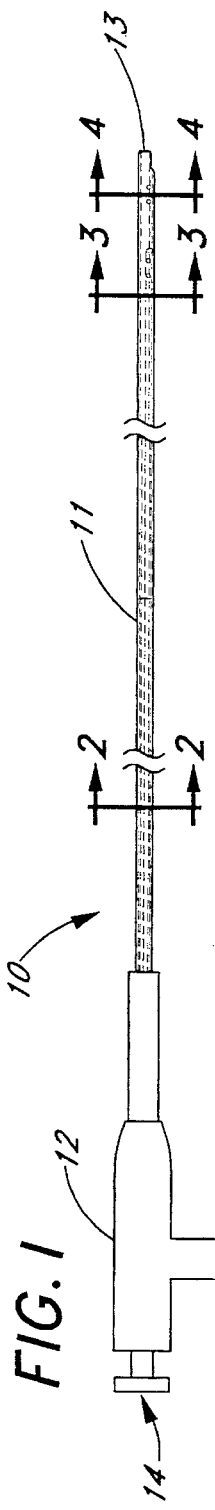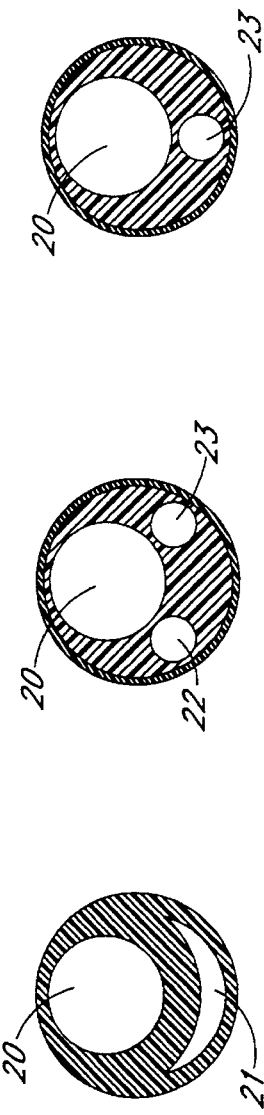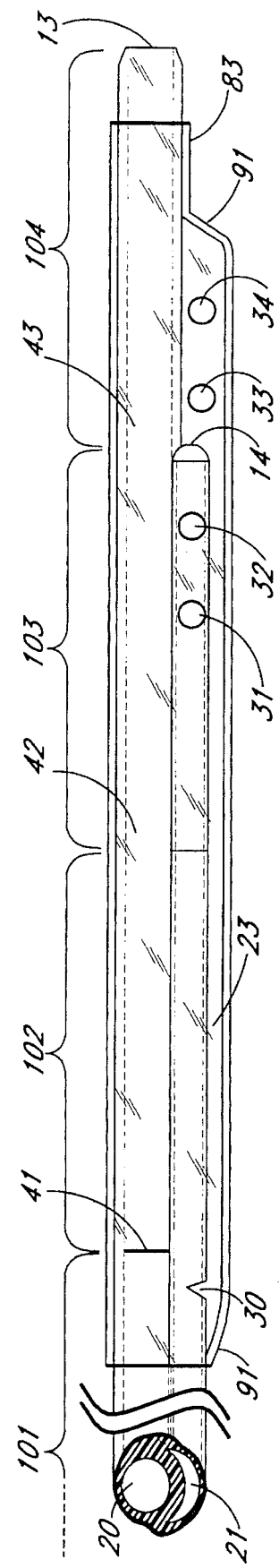

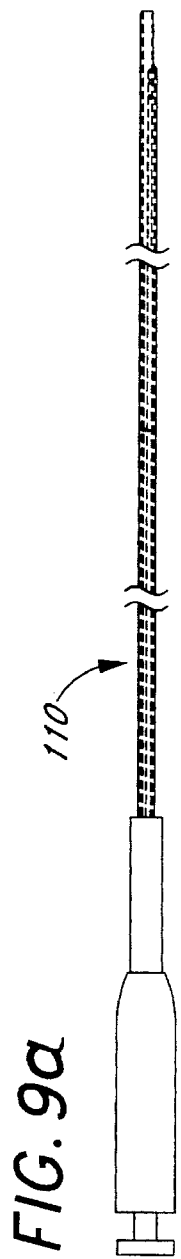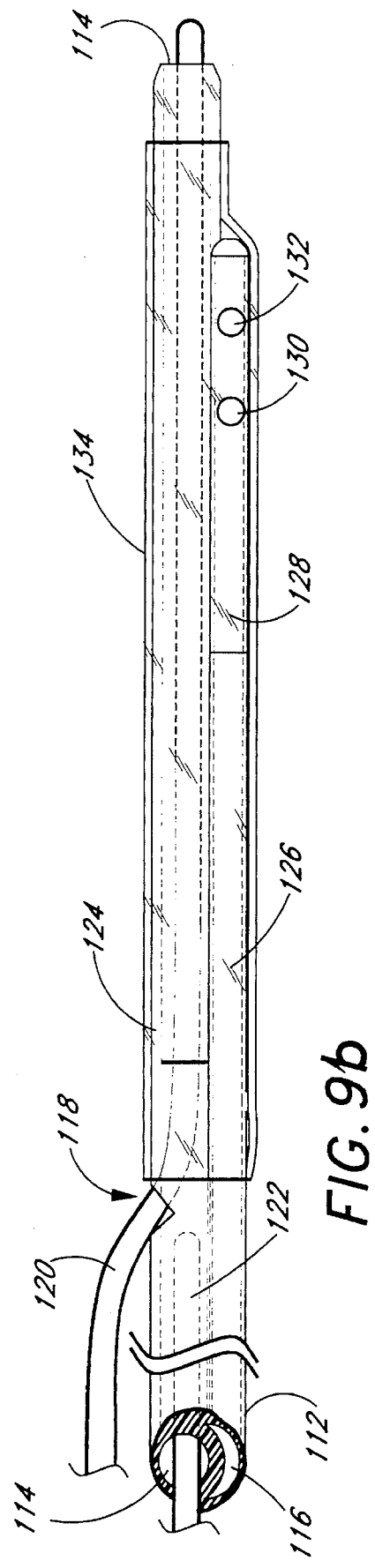

LOW PROFILE INFUSION CATHETER

This application is a continuation of U.S. patent application Ser. No. 08/083,021 filed Jun. 24, 1993, now abandoned.

FIELD OF THE INVENTION

This invention relates to medical infusion catheters, and, in particular, low profile infusion catheters having multiple zones of differing flexibility.

BACKGROUND OF THE INVENTION

Myocardial infarctions are one of the leading causes of death in the United States. As reported in Harrison, Principles of Internal Medicine (12th Ed. 1991) Vol. 1 at 953, approximately 1.5 million myocardial infarctions are reported to occur each year in the United States, alone. As much as 25 percent of persons suffering an acute myocardial infarction have been reported to die shortly after the episode. Of those 25 percent, about half die before reaching a hospital.

The mortality rate from myocardial infarction tells only part of the story, however. For every person that dies of a myocardial infarction, three persons survive their episode. A large portion of the survivors sustain irreversible damage to their heart muscle leaving them with reduced cardiac function. This disability decreases their quality of life and their life expectancy, and is a major contributor to the cost of health care in the United States and other countries.

Myocardial infarctions cause death and disability by two primary mechanisms. First, damaged heart muscle is subject to a variety of electrical disturbances collectively known as "arrhythmias." These arrhythmias can cause sudden death, syncopal episodes or lead to ischemic episodes in other organs including the brain. Secondly, damaged heart muscle does not regenerate to any appreciable degree (unlike skin or liver tissue) such that dead heart muscle permanently looses its contractile nature. As the heart looses its ability to contract, the person becomes more restricted in his activities of daily living. At some degree of loss, depending on the location of the dead muscle, the heart will pass a critical point leading to pump failure and death.

Myocardial infarctions have several known causes. Most commonly, they are the result of vasospastic episodes in the coronary arteries, emboli to the coronary arteries, thrombi in the coronary arteries, or a combination of vasospasm, emboli and thrombi. Two of the three common causes, emboli and thrombi, are clots formed to varying degrees of cells and cellular debris, platelets, products of the coagulation system, and cholesterol, triglycerides and other fats.

The ideal management for myocardial infarctions is prevention. There is major ongoing research into methods of prevention and there has been significant progress in decreasing the incidence of myocardial infarction in recent years. However, treatment of myocardial infarctions once they have occurred is still a mainstay of management.

Traditionally, treatment of myocardial infarctions took the form of bed rest, oxygen and analgesics. More recently, invasive and non-invasive monitoring combined with effective anti-arrhythmics have decreased the rates of morbidity and mortality. Further, drugs have been developed which alter vascular tone and the contractile state of the remaining normal heart muscle to prevent and treat pump failure.

One recent advance in treatment has been attempt to restore vascular patency in the occluded arteries. This has been done by surgical means through coronary artery bypass grafting, mainly in situations where occlusion was imminent but not complete. Similarly, percutaneous transluminal coronary angioplasty has been performed in such situations using balloons, burrs and lasers. In addition, some progress has been made with various drug therapy approaches, using drugs which dissolve products of the coagulation system, sometimes referred to as "thrombolytic" drugs.

A variety of efforts have been made to design catheters for delivering thrombolytic or other intravascular drugs. For example, U.S. Pat. No. 5,087,244 to Wolinsky et al. discloses a catheter having a perforated inflatable balloon for expressing drug to the vascular wall. U.S. Pat. No. 5,021,044 to Sharkawy discloses an infusion catheter having a plurality of effluent flow ports along its outer wall, each having a successively larger diameter in the distal direction.

U.S. Pat. No. 4,968,307 to Dake et al. discloses another catheter for infusion of therapeutic fluids, in which each effluent flow port through the wall of the catheter is placed in fluid communication with a fluid source by a unique flow passageway extending throughout the length of and within the wall of the catheter body.

Notwithstanding the foregoing, there remains a need for a low profile infusion catheter for delivering thrombolytic drugs to a preselected site, with improved flexibility characteristics and relatively uniform delivery over a preselected axial length.

SUMMARY OF THE INVENTION

In accordance with one aspect of the present invention, there is provided an infusion catheter for infusing a medication at a predetermined site in a body lumen. The catheter comprises an elongate tubular body, having at least one proximal fluid lumen extending through a proximal zone of the tubular body. A branch point is provided in the proximal fluid lumen at which said proximal fluid lumen divides into at least a first and a second distal fluid lumen.

At least a first effluent port is provided in fluid communication with the first distal fluid lumen, and at least a second effluent port is provided in communication with the second distal fluid lumen. Preferably, the infusion catheter comprises two or more effluent ports on each of said first and second distal lumens.

In accordance with a further aspect of the present invention, there is provided a catheter having multiple discrete zones of flexibility. The catheter comprises an elongate flexible tubular body, having a first zone on the body with a substantially uniform flexibility throughout. A second zone is provided on the body, having a substantially uniform flexibility throughout that differs from the flexibility of the first zone. At least a portion of the second zone comprises two elongate tubular bodies joined side by side such that the longitudinal axis of each of the two tubular bodies is generally parallel to each other. Preferably, at least one additional flexibility zone is provided on the catheter, having a flexibility that differs from the flexibility of the first and second zones.

In one embodiment of the invention, a catheter is provided having at least three zones of discrete flexibility. The first zone comprises a continuous extrusion having at least one lumen extending axially therethrough. The two elongate tubular bodies of the second zone preferably comprise different construction materials. In a preferred embodiment, the first flexibility zone comprises a high density polyethylene extrusion. At least one of the additional flexibility zones comprises a high density polyethylene extrusion component and a relatively more flexible polymer component.

In accordance with a further aspect of the present invention, there is provided an infusion catheter having both the infusion manifold and discrete flexibility zone features incorporated therein. The catheter comprises an elongate tubular body having at least one proximal fluid lumen extending through a proximal zone of the tubular body. A branch point is provided in the proximal fluid lumen at which the proximal fluid lumen divides into two or more distal fluid lumens. At least a first effluent port is provided in fluid communication with a first distal fluid lumen, and at least a second effluent port is provided in fluid communication with the second distal fluid lumen.

The proximal zone of the tubular body has a first degree of flexibility, and the tubular body has at least two discrete distal zones of flexibility distal to the proximal zone.

In accordance with a further aspect of the present invention, there is provided a method of treating an intravascular site. The method comprises the steps of advancing a guidewire through a patient's vasculature until reaching an area close to the site, and advancing an infusion catheter over the guidewire until a distal end of the infusion catheter extends into an area close to the site.

The infusion catheter comprises an elongate tubular body having at least one proximal fluid lumen extending through a proximal zone of the tubular body, and a branch point in the proximal fluid lumen at which the proximal fluid lumen divides into at least two distal fluid lumens. At least a first effluent port is provided in communication with a first distal fluid lumen. Preferably, at least a second effluent port is provided in fluid communication with the second distal fluid lumen.

Medication is thereafter introduced through said proximal fluid lumen to discharge the medication through the effluent ports.

Further features and advantages of the present invention will become apparent to one of skill in the art in view of the detailed description of preferred embodiments which follows, when considered together with the attached drawings and claims.

BRIEF DESCRIPTION OF THE DRAWINGS

FIG. 1 is an elevational view of a catheter embodying features of the invention;

FIG. 2 is an enlarged cross-sectional view taken along lines 2—2 of FIG. 1;

FIG. 3 is an enlarged cross-sectional view taken along lines 3—3 of FIG. 1;

FIG. 4 is an enlarged cross-sectional view taken along lines 4—4 of FIG. 1;

FIG. 8 is an enlarged view of the distal end of the catheter at the completion of manufacture;

FIG. 9a is an elevational view of an alternate embodiment of the invention in a monorail type design; and FIG. 9b is an enlarged view of the distal end of the embodiment shown in FIG. 9a.

DETAILED DESCRIPTION OF PREFERRED EMBODIMENTS

Figure 5:
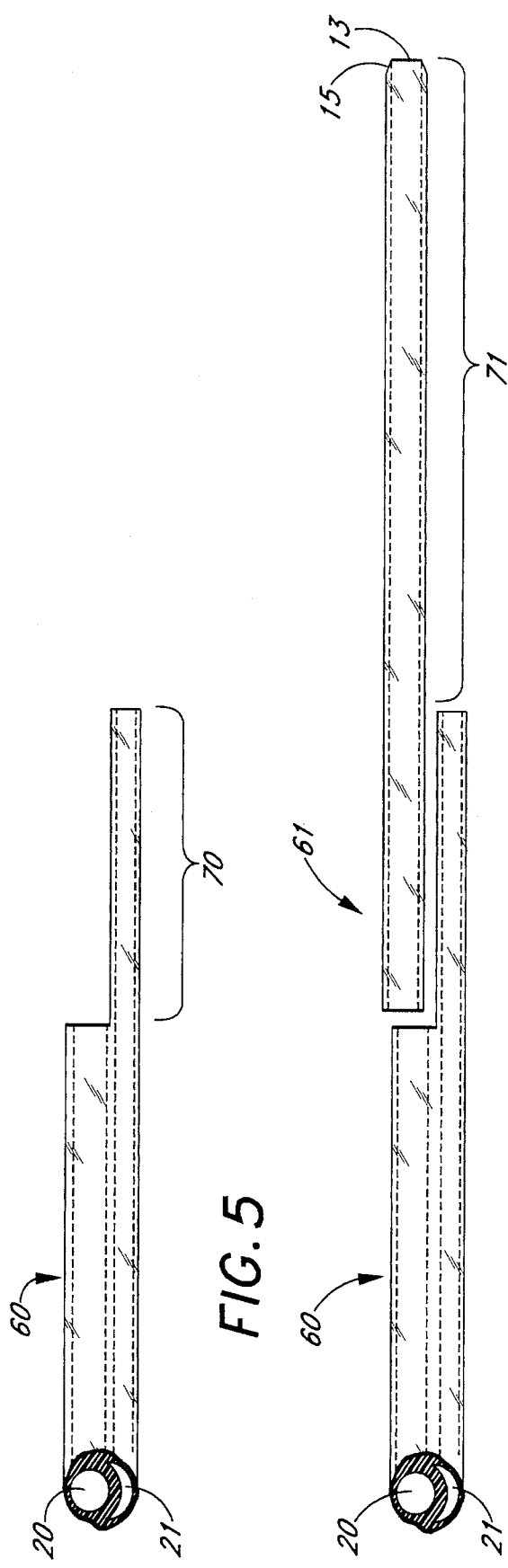
FIG. 5 is an enlarged view of the junction of the first and second zones of flexibility of the catheter at Stage 1 of the manufacture.

Drugs which dissolve products of the coagulation system are referred to as "thrombolytic drugs," "thrombolytic agents" or simply "thrombolytics." There are three thrombolytics currently in use: 1) streptokinase, 2) urokinase, and 3) tissue plasminogen activator (tPA). These drugs act to dissolve certain components of clots, effectively breaking up the clots.

There is currently enough experience with thrombolytics to know that they reduce the in-hospital mortality rate from myocardial infarctions significantly. To be effective, they must be administered as soon as possible after the clot has occluded the coronary artery. Delay in administering thrombolytics causes a rise in the morbidity and mortality from myocardial infarctions. After about 24 hours, thrombolytics cease to be an effective treatment.

Like all medical treatments, thrombolytics have their problems. First, as noted, time is of the essence in administration. Secondly, thrombolytics are not specific for clots in the coronary arteries. Hence, they will dissolve whatever clots they encounter causing hemorrhage, most ominously, in the brain and gut. Third, they are expensive.

There are two potential modes to address these problems; developing new thrombolytic agents and developing new modes of administration. As can be readily appreciated from the above discussion, the ideal mode of administration would have the following properties: 1) direct access to the clot site to minimize the exposure of other tissues to the thrombolytic and increase the concentration of the thrombolytic at the clot site, and 2) use of the smallest quantity of drug possible to minimize exposure of other tissues to the thrombolytic and to minimize cost of the drug, and 3) rapid administration.

Because of the need for rapid administration and uncertainty of the exact location of the clot, thrombolytics have in the past generally been administered by the peripheral intravascular route. This route is easy to access, inexpensive to access and, most importantly, rapid to access. The main problem has been that, using this route exposes all body tissues to the thrombolytic. Hence, thrombolytics are contraindicated in circumstances where bleeding is likely and potentially critical, such as in recent surgery, strokes or bleeding ulcers. Even where these risk factors are not present, peripheral intravascular administration of thrombolytics are associated with a baseline rate of hemorrhage. An alternate mode of administration which could deliver small quantities of thrombolytics more directly to the clot, would tend to avoid secondary bleeding while allowing increased concentrations of the thrombolytic where it is needed.

The present invention addresses the problems inherent with thrombolytic delivery by incorporating two features into an infusion catheter. First, the catheter has a series of discrete zones of flexibility which can be made to differ from one another in a pattern customized for the intended use. These flexibility zones allow the catheter to access remote intravascular spaces and body lumens, in combination with insertion over a guidewire or without insertion over a guidewire, in a manner superior to catheters without such discrete zones of flexibility.

Secondly, multiple effluent port embodiments of the present catheter incorporates distal fluid lumens which branch off a common proximal lumen. The effluent ports in the distal fluid lumens are arranged in a manner that increases the uniformity of the delivery of medication external to the catheter, while minimizing the catheter profile.

These features provide a superior catheter for the delivery of thrombolytics because 1) they allow more rapid access to remote clot sites than is available with conventional catheters, 2) the thrombolytics are delivered just upstream from the clot and relatively small quantities are needed, minimizing exposure of non-target tissues to the thrombolytics, and 3) cost of the drug is minimized because relatively small quantities are needed. Hence, the present invention directly addresses the problems inherent with thrombolytic delivery as discussed above. In addition, the multiple lumen design minimizes the catheter profile and permits access to relatively remote vascular sites.

It is anticipated that both the multiple discrete zones of flexibility and the improvement in delivery of a uniform concentration of fluid will have applications beyond the delivery of thrombolytics in coronary arteries. The same features will obviously be useful in the delivery of thrombolytics in peripheral and intra-cranial clots. Further, the catheter of the present invention is useful for delivering any of a variety of non thrombolytic agents such as chemotherapeutic medications, hyper or hypo-osmolar fluids, acidic or alkaline solutions, solutions requiring a high or low temperature during use, concentrated saline solutions, or others.

Also, a catheter having multiple discrete zones of flexibility may have uses in difficult to access body lumens, such as the biliary tree, eustachian tubes, fallopian tubes, urethra and ureters, cerebral spinal fluid system, pancreatic ducts, as well as more general pediatric or fetal uses. This is particularly true where guidewires are dangerous such as in delicate vasculature or around hypertrophied prostate.

Referring to FIGS. 1–4 and 8, there is illustrated one embodiment of the catheter assembly for intravascular delivery. The catheter assembly 10 generally includes an elongated catheter body 11 with an adapter 12 at its proximal end, and an atraumatic distal tip 13. The elongated catheter body has, in an "over the wire" embodiment, an axial guidewire lumen 20 extending from an introduction port 14 throughout the length of the catheter body 11.

The catheter body 11 has at least one proximal fluid lumen 21 for providing fluid communication between a proximal infusion port 18 and one or more distal delivery ports as discussed infra.

In the illustrated, multi lumen embodiment, proximal fluid lumen 21 divides into at least two distal lumens. In the embodiment shown, the two distal lumens are depicted schematically as a first distal lumen 22 and a second distal lumen 23. The schematic nature of these illustrations, particularly FIG. 3 will become apparent from the preferred method of manufacturing discussed infra.

The point of communication or manifold between the proximal fluid lumen 21 and the distal fluid lumens 22 and 23 is shown in the configuration of a notched opening 30 through the wall of the catheter body 11. Thus, a first portion of the medication or other infusate traveling distally through proximal lumen 21 advances down distal branch lumen 22 and escapes via one or more effluent ports 31 and 32. A cap or other closure means seals the distal end of branch lumen 22, as will be discussed. A second component of the infusion fluid advances through opening 30 and into a second distal branch lumen 23. Branch lumen 23 conducts the fluid to one or more effluent ports 33 and 34. In a single lumen embodiment, the opening 30 is deleted and other minor alterations are made during the method of manufacture, discussed infra.

The distal fluid lumens discharge external to the catheter through one or more distal effluent ports. The ports in fluid communication with the first distal fluid lumen 22 are labeled 31 and 32 and the ports in fluid communication with the second distal fluid lumen 23 are labeled 33 and 34. Depending upon the intended application, more or less than two effluent ports can be readily provided for each of the distal fluid lumens.

For example, in an alternative embodiment, a single effluent port 31 provides fluid communication between distal lumen 22 and the exterior of the catheter. In addition, a single effluent port 33 provides fluid communication between distal lumen 23 and the exterior of the catheter. Alternatively, three or more effluent ports can be provided for each of the distal fluid lumens 22, 23, or more. However, it has been determined by the present inventors that excessive effluent flow ports in a single distal lumen produces a relatively uneven delivery profile along the delivery length of the catheter which may be undesirable for certain applications.

The precise location of effluent flow ports can be varied considerably, depending upon the intended application of the catheter. In the illustrated embodiment, the flow ports 31, 32, 33 and 34 are illustrated as substantially aligned along an axis parallel to the longitudinal axis of the catheter. Alternatively, each successive flow port can be spaced radially apart from the prior flow port to provide a spiral flow port configuration. The flow ports can be positioned on opposite sides of the catheter, if desired, as will be apparent to one of skill in the art.

The flow ports define an infusion zone on the catheter, which can be varied in length depending upon the intended application. In some applications, the axial length of the infusion zone approximates the length of the lesion or other site to be treated. In general, the length of the infusion zone for these applications will fall within the range of from the width of a single flow port to about 16 cm. Preferably, the infusion zone is about four or five cm long with four flow ports 31, 32, 33 and 34 equally spaced within the zone.

The position of the infusion zone on the catheter 10 can also be varied depending upon the intended application. Preferably, the infusion zone will be located on a distal region of the catheter, and most preferably within about 10 cm of the distal end. In one preferred embodiment, the proximal most flow port 31 is positioned within about 4 cm of the distal end 13 of the catheter 10.

In general, medication or other infusate is delivered through the flow ports at a low pressure, to minimize the possibility of trauma to the adjacent vascular intima. Thus, the sum of the cross sectional flow areas of the flow ports will generally exceed the cross sectional flow area of the proximal fluid lumen 21. In addition, the sum of the cross-sectional flow areas of the distal lumens is generally greater than the cross-sectional area of the proximal lumen. For example, one embodiment of the present invention having a proximal lumen 21 with a diameter of about 0.013 inches is provided with two distal lumens 22 and 23, each having a diameter of about 0.010 inches. Internal diameters of much less than about 0.010 inches permit only relatively low flow rates and require relatively higher back pressure. The interior diameter of any of the lumens described herein can generally be larger than the specific embodiments disclosed; however, larger interior diameters result in a larger external profile of the catheter.

In addition, in the two lumen, four flow port embodiment illustrated in FIG. 8, the applicants have determined that a slight increase in cross sectional area of each successive flow port in the distal direction on a given distal lumen produces an improved (i.e., more uniform) fluid delivery profile over the delivery area of the catheter. For example, in an embodiment of the catheter as illustrated in FIG. 8 in which the cross sectional flow area of distal lumen 22 corresponds to the flow area of a cylindrical lumen having a 0.010 inch diameter, a proximal flow port 31 having a 0.008 inch diameter and a distal flow port 32 having a 0.010 inch diameter was found to produce a relatively uniform effluent fluid flow. This same principal is found to apply to the second lumen 23, in which, as will be apparent from the method of manufacture, the cross section of the flow path in lumen 23 is more accurately described in terms of area than diameter.

In other embodiments, the cross-sectional shape of the fluid lumens may be any shape, including circular, semi-circular triangular or other. There may be more than one proximal fluid lumen or more than two distal fluid lumens and more than one point of communication between the proximal and distal fluid lumens. The number of distal ports, their location and their cross-sectional shape can also vary depending upon the manufacturing process and intended use of the catheter.

In addition to the foregoing, the catheter 10 is preferably provided with a series of discrete zones of flexibility. Four zones are shown in the embodiment depicted in FIG. 8. From proximal to distal, they are 101, 102, 103 and 104. The junction between zones 101 and 102 is 41. The junction between zones 102 and 103 is 42. The junction between zones 103 and 104 is 43. In general, the flexibility zones 101, 102, 103 and 104 each have increasing flexibility in the distal direction as described infra.

Reference is made to FIGS. 5–8 which illustrate the stages in manufacture of one embodiment of a four flexibility zone infusion catheter. All suggested dimensions and materials are for an embodiment suitable for the delivery of thrombolytics into an intravascular area of a coronary artery clot. Different dimensions and materials may also be used as will be apparent to one of skill in the art.

In Stage 1, a tubular body 60, typically between about 120 and 130 centimeters long, and having an outside diameter of about 3.0 French is provided. The tubular body has a central guidewire lumen 20 with an inside diameter of approximately 0.018 inches. At least one fluid lumen 21 is provided, with a cross-sectional area of approximately 0.000133 square inches. The tubular body 60 is formed through extrusion processes well known to those skilled in the art, using medical grade, sterilizable polymers such as high density polyethylene (HDPE).

Next, the distal portion of the tube 60 containing the guidewire lumen 20 is cut back to leave a distally extending segment 70 of the portion of the tube 60 containing the fluid lumen 21. FIG. 5 depicts the catheter at the end of Stage 1. Segment 70 provides a conduit for fluid lumen 22, as well as a structural component of the flexibility zone 102. In an alternate embodiment, where fewer flexibility zones are desired, the distally extending segment 70 can be shortened or deleted. In its place, fluid lumen 22 can be formed in a manner similar to fluid lumen 23. This is accomplished, for example, by heat shrinking an outer tubular sleeve around two separate removable mandrels, spaced apart from each other and extending generally parallel to the longitudinal axis of the catheter body.

Figure 6:
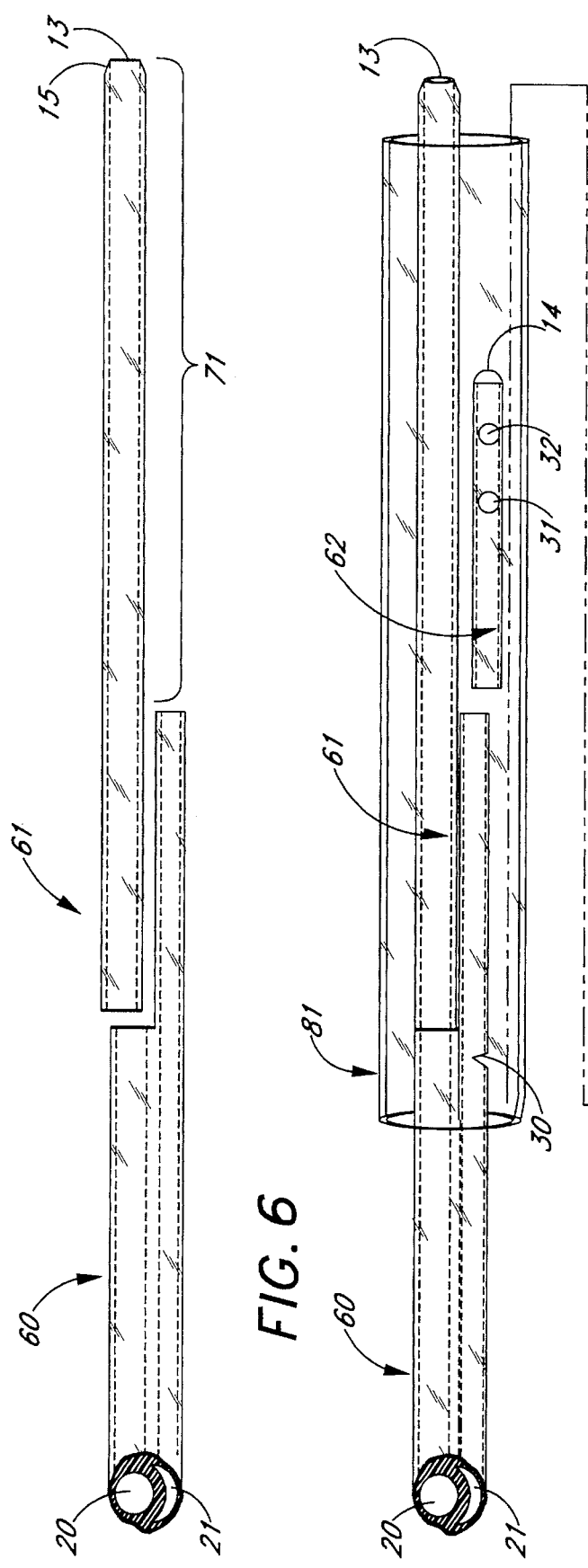
FIG. 6 is an enlarged view of the junction of the first and second zones of flexibility of the catheter at Stage 2 of the manufacture.

In Stage 2, depicted in FIG. 6, a separate tube 61 comprising a flexible material such as a medium or low density polyethylene is provided. Tube 61 is preferably approximately 15 centimeters long. However, other lengths can be readily adapted, depending upon the desired flexibility characteristics of the catheter. Tube 61 preferably has an outside diameter of about 0.021 inches and a central lumen with an inside diameter of about 0.016 inches is provided. These dimensions can be varied depending upon the desired external profile and the guidewire diameter.

Tube 61 may be formed through an extrusion process and is preferably provided at its distal end with a bevel 15 to minimize trauma during introduction. Tube 61 is positioned onto the distal end of and coaxially with the guidewire lumen 20 of tube 60. The distal portion 71 of tube 61 extends approximately 10 centimeters past the distal end of the fluid lumen 21.

Figure 7:
FIG. 7 is an enlarged view of the distal end of the catheter at Stage 3 of the manufacture.

In Stage 3, depicted in FIG. 7, a separate tube 62 composed of medium or low density polyethylene is provided. Tube 62 is approximately 5 centimeters long with an outside diameter of about 0.21 inches and a central lumen having an inside diameter of about 0.016 inches. Tube 62 is formed through conventional extrusion processes and may be plugged or sealed at the distal end 14, or sealed following removal of a mandrel as discussed infra. Tube 62 is then positioned at the distal end of the fluid lumen 21 on tube 60.

An opening 30 is cut into tube 60 exposing fluid lumen 21 but not the guidewire lumen 20. A triangular opening 30 is depicted in FIG. 7 such as may be formed by notching, but the opening 30 can be any of a variety of shapes.

A mandrel 80 having a length of approximately 20 centimeters and 0.010 inches in diameter is placed against the outer surface of tube 60, tube 61 and tube 62, such that the proximal end of the mandrel is positioned at or proximal to opening 30. Mandrel 80 extends distally past the ports 31 and 32, and generally beyond the distal end of the assembly to provide a convenient handle. The mandrel may have any of a variety of cross-sectional shapes including round, triangular or semi-circular. The mandrel may also have a progressively altering cross-sectional shape to create a distal fluid lumen with a varying cross-sectional shape from its proximal to distal end. Preferably, the mandrel is provided with a teflon coating or release agent such as silicone to facilitate removal as will be described.

Preferably, a second mandrel, having a diameter of about 0.016 inches is positioned within tube 61 to maintain patency of the lumen during the next manufacturing steps. Similarly, a third mandrel having a diameter of about 0.010 inches is positioned within tube 62.

A shrinkable tubular sheath 81 is provided for shrinking onto the various catheter components to produce the final assembly. In one embodiment, sheath 81 is approximately 15 to 20 centimeters long and has a wall thickness of about 0.001 inches. Such tubing is preferably made from a heat shrinkable material such as medium or low density polyethylene. Sheath 81 is positioned around the assembly comprising tubes 60, 61 and 62, and the mandrels. Sheath 81 is thereafter heat shrunk around the catheter assembly. The mandrels are thereafter withdrawn to produce distal lumen 22, and preserve guidewire lumen 20 and infusion lumen 23. A distal section 83 of sheath 81 is then sealed such as by additional heat shrinking, to the catheter body.

Thus, in accordance with one aspect of the present invention, a low profile catheter body structure is provided. This structure can be utilized in the construction of infusion catheters such as those disclosed herein, or other catheters in which one or more fluid lumen are desired, and the outer profile of the catheter is to be minimized. In accordance with this feature of the invention, a catheter or catheter subassembly is constructed having at least one structural component. In the illustrated embodiment, that structural component can be a tube such as 61, or a combination of structural components such as tube 61 and distal extension 70 from catheter body 60. Conveniently, tube 61 defines a central pathway for receiving a guidewire, as is conventional with vascular catheters.

One or more mandrels are then positioned adjacent the structural component, and surrounded by a heat shrinkable material. Such materials are conveniently available for use in the construction of angioplasty dilatation balloons. The heat shrink material is there after exposed to a sufficient duration and level of heat to shrink the material around the one or more mandrels, and around the structural component of the catheter assembly. Thereafter, one or more mandrels are axially withdrawn, leaving one or more discrete axially extending fluid lumen in the catheter assembly. The open distal or proximal end of the lumen, depending upon which direction the mandrel is withdrawn, can thereafter be sealed, connected to source or effluent structures as desired.

Catheters in which one or more central lumen are formed within a shrink wrap tubing have a minimal exterior diameter. In general, conventional catheters are formed by extrusion processes, which do not ordinarily permit a wall thickness of less that about 0.002 inches. Medium or low density polyethylene balloon material, however, is readily available having a wall thickness on the order of about 0.001 inches. This structure can result in significant minimization of total catheter diameter, particular in a catheter having multiple internal lumens. As will be apparent to one of skill in the art, the shrink wrap fluid lumens of the present invention can be provided in a catheter with or without a manifold as disclosed elsewhere herein, as well as with or without infusion capabilities of the type disclosed herein.

As will be apparent from the foregoing structure, the catheter body subassembly of the present invention may have two different exterior diameters. A first, deflated diameter can exist such as for insertion and positioning of the catheter at a particularly remote location in a body lumen. Following positioning, and during infusion of mediation or pressurization of the catheter lumen for other purposes, the catheter lumens formed in accordance with the foregoing procedures will inflate to their second, operating diameter. In this manner, a multiple lumen catheter can be readily provided having a first, insertion diameter of only slightly larger than the diameter of the structural component of that catheter. After positioning, the catheter will tend to have a second, inflated diameter such as might occur during infusion or other use of the central inflatable lumen.

The result of the final stage, Stage 4, is depicted in FIG. 8. At least one and preferably two effluent ports 33 and 34 having diameters of approximately 0.008 and 0.010 inches, respectively, are made in the distal end of the sheath 81 by drilling, creating external fluid communication with the distal fluid lumen 23 bounded by the sheath 81. At least one and preferably two effluent ports 31 and 32 providing external fluid communication with the distal fluid lumen 22 are also provided.

Although the various components of the catheter are described above as being held in place by an outer shrink wrap 81, other means for securing catheter components can readily be adapted for use in the present invention. For example, tubular components 60, 61 and 62 can be heat bonded, solvent bonded, irradiated or provided with any of a variety of other securing means to provide a unitary structure. Outer jacket 81 can be provided such as by wrapping, dipping or spraying operations, as can be readily devised by one of skill in the art in view of the disclosure herein.

The effect of the above method of manufacture is to create a catheter having several discrete zones of flexibility and having distal effluent ports that are supplied by distal fluid lumens branching off a common proximal fluid lumen. The different zones of flexibility 101, 102, 103 and 104 are provided largely by different combinations of materials while maintaining a generally consistent exterior profile throughout. The most proximal zone 101 generally extends from the adapter 12 to the interface 41. In a typical coronary artery infusion catheter, this segment will be on the order of about 130 cm or longer. For manufacturing convenience, the proximal segment 101 preferably comprises a homogenous extrusion of a first material throughout, such as the relatively rigid HDPE.

The next segment 102 comprises an extension 70 of the first material disposed adjacent a tubular section 61. Tubular section 61 generally comprises a more flexible material than the first material of segment 101, such as medium or low density polyethylene. The combination of segment 70 and tube 61 within flexibility zone 102 is thus a slightly more flexible aggregate catheter body than section 101.

Flexibility zone 103 comprises a portion of tube 61, together with tube 62. Tube 62 is also more flexible than extension 70, so that the combination of tube 62 and tube 61 produces a slightly more flexible zone 103.

Distal most flexibility zone 104 comprises a section of tube 61, having only the outer jacket or shrink wrap layer 81 disposed thereon. This is the most flexible or floppy portion of the infusion catheter. If desired, the outer shrink wrap jacket can extend distally beyond tube 61 to provide a highly floppy tip.

Variations in the method of manufacture are anticipated where the catheter will be used to deliver thrombolytics to a specific area in or near a coronary artery, or where the catheter will be used for purposes other than the delivery of thrombolytics to the area of a clot in a coronary artery. These variations include increasing or decreasing the number or lengths of zones of flexibility, varying the specific flexibility of the zones, increasing the number of proximal fluid lumens, distal fluid lumens, points of communication between the proximal and distal fluid lumen, number and arrangement of the effluent ports and the cross-sectional area and shape of the components of the catheter. In addition, although the structural components of the catheter body disclosed herein have all been identified as comprising a polymeric material, many of these components can also be constructed utilizing conventional spring coil tubular bodies as is well known in the catheter or guidewire art.

Referring to FIGS. 9a and 9b, there is disclosed an infusion catheter in accordance with a further aspect of the present invention, illustrating both a single fluid flow lumen embodiment and a monorail type (rapid exchange) adaptation of the infusion catheter. Infusion catheter 110 generally comprises an elongate flexible tubular proximal body 112 as has been previously discussed. Proximal body 112 is provided with an axially extending guidewire lumen 114, and at least one infusion lumen 116.

An opening 118 is provided in the wall of the catheter body 112, for providing access to guidewire lumen 114.

Opening 118 can be positioned in any of a variety of positions along the length of the catheter 110 and is preferably within about the most distal 15 or 30 cm of the catheter.

In the illustrated embodiment, the portion of the guidewire lumen 114 disposed proximally to opening 118 is occluded or filled with a support member 122. The support member 122 can be a guidewire or other member for filling the guidewire lumen 114 to improve the pushability and flexibility characteristics of the catheter body. Alternatively, the proximal portion 112 of catheter 110 can be formed without a guidewire lumen 114, as will be apparent to one of skill in the art.

In use, a conventional guidewire 120 extends through opening 118 and into the guidewire lumen 114. Guidewire 120 extends distally through lumen 114 and out the distal end of the catheter as is known in the art. The distal most section of guidewire lumen 114 is preferably provided within a discrete tubular element 124, which is analogous to tube 61 discussed in previous embodiments.

Similarly, a distal extension 126 of proximal extrusion 112 facilitates the stepped flexibility as discussed in connection with the previously disclosed embodiments. The central lumen 116 extending through extension 126 is placed in fluid communication with a further tube 128 which is provided with one or more flow ports 130, 132. An outer tubular jacket 134 is preferably heat shrunk or otherwise applied to the catheter assembly, to produce a final infusion catheter.

In accordance with this embodiment, the second infusion lumen 23, together with opening 30 (illustrated in FIG. 8) have been deleted, to provide a single infusion lumen design. As will be apparent to one of skill in the art, the embodiment of FIG. 8 can be provided in a monorail configuration as disclosed in FIGS. 9a and 9b, and the monorail configuration can also be provided with a manifold leading to two or more infusion lumens such as 22 and 23.

In a typical procedure, a guidewire is sterilely introduced into the femoral artery of a patient having a known, recently formed, clot in a coronary artery via techniques well known to those skilled in the art. The guidewire is then advanced to the region of the clot and the catheter threaded over the guidewire. The guidewire can remain in place or be withdrawn to allow the catheter to advance using the inherent flexibility zones of this design to maneuver intravascularly.

A thrombolytic agent is selected by criteria of the treating institution. The thrombolytic is introduced with a carrier fluid into the proximal fluid lumen and is made to flow by gravity or with an externally supplied pressure. The thrombolytic passes through the proximal lumen and divides at the opening into the distal lumens and onto the distal portion of the catheter.

The thrombolytic is discharged through the series of effluent ports in the distal fluid lumens such that fluid exiting, at least, some linearly adjacent ports has travelled through different distal fluid lumens which branched off a common proximal lumen. The effect is to create a more uniform delivery of thrombolytic external to the catheter than would be present without the proximal lumen branching into multiple distal lumens.

Dye may be introduced through the guidewire lumen during the process, to determine patency of the diseased vessel. After patency is restored, the guidewire can be reinserted, the catheter removed, and a conventional balloon angioplasty, rotational arthrectomy or laser angioplasty threaded over the guidewire to alleviate the remaining or underlying lesion.

Although the present invention has been described in terms of certain preferred embodiments, other embodiments can be readily devised by one skill in the art in view of the foregoing, which will also use the basic concepts of the present invention. Accordingly, the scope of the present invention is to be defined by reference to the attached claims.

I claim:

1. An infusion catheter, comprising:
   an elongate tubular body extending from a proximal end to a distal end in a distal direction;
   at least one proximal, fluid lumen extending through a proximal zone of said tubular body;
   a branch point in said proximal, fluid lumen at which said proximal, fluid lumen divides into at least a first and a second distal fluid lumen;
   at least a first effluent zone on the tubular body in fluid communication with the first distal fluid lumen; and
   at least a second effluent zone on the tubular body in fluid communication with the second distal fluid lumen;
   said second distal fluid lumen having a distal portion extending farther in said distal direction than said first distal fluid lumen, said distal portion containing at least a portion of said second effluent zone.

2. An infusion catheter as in claim 1, comprising two or more effluent ports on each of said first and second effluent zones.

3. An infusion catheter as in claim 1, comprising two distal, fluid lumens and two effluent ports on each of said distal fluid lumens.

4. An infusion catheter as in claim 1, further comprising a guidewire lumen extending axially through at least a portion of said infusion catheter.

5. An infusion catheter, comprising:
   an elongate tubular body;
   at least one proximal, fluid lumen extending through a proximal zone of said tubular body;
   a branch point in said proximal, fluid lumen at which said proximal, fluid lumen divides into two or more distal, fluid lumens;
   a first effluent zone including at least one port in fluid communication with a first, distal fluid lumen; and
   a second effluent zone including at least one port in fluid communication with a second, distal, fluid lumen,
   the most proximal port in the second distal lumen is displaced distally along the tubular body from the most distal port in the first distal lumen.

6. An infusion catheter as in claim 5, further comprising a guidewire lumen extending axially through at least a portion of said infusion catheter.

7. An infusion catheter as in claim 5, comprising two distal, parallel fluid lumens and two effluent ports on each distal, fluid lumen.

8. An infusion catheter, comprising:
   an elongate tubular body;
   at least one fluid lumen extending through a proximal portion of the tubular body;
   a branch point in said fluid lumen at which said fluid lumen divides into at least a first and a second branch;
   an intermediate portion of the tubular body extending distally from said branch point to a distal end of the first branch, and containing the first and second branches; and a distal portion of the tubular body extending distally from the distal end of the first branch, and containing the second branch;

said intermediate portion containing a first effluent zone in the first lumen and said distal portion containing at least a portion of a second effluent zone.

9. An infusion catheter as in claim 8, wherein the cross sectional area through the intermediate portion of the tubular body is greater than the cross sectional area through the distal portion of the tubular body.

10. An infusion catheter as in claim 8, further comprising a guidewire lumen extending axially through at least a portion of said infusion catheter.

\* \* \* \* \*

UNITED STATES PATENT AND TRADEMARK OFFICE
CERTIFICATE OF CORRECTION

PATENT NO. : 5,569,215
DATED : October 29, 1996
INVENTOR(S) : Michael Crocker

It is certified that error appears in the above-indentified patent and that said Letters Patent is hereby corrected as shown below:

Column 13, line 5, change "lumen" to --branch--.

Signed and Sealed this

Eighth Day of April, 1997

Attest:

BRUCE LEHMAN

Attesting Officer

Commissioner of Patents and Trademarks